(12) United States Patent
Tateishi

(10) Patent No.: US 10,070,797 B2
(45) Date of Patent: Sep. 11, 2018

(54) MEASURING APPARATUS, PROBE PORTION, AND CONNECTING CABLE

(71) Applicant: PIONEER CORPORATION, Kanagawa (JP)

(72) Inventor: Kiyoshi Tateishi, Kanagawa (JP)

(73) Assignee: PIONEER CORPORATION, Kanagawa (JP)

( * ) Notice: Subject to any disclaimer, the term of this patent is extended or adjusted under 35 U.S.C. 154(b) by 299 days.

(21) Appl. No.: 14/648,766

(22) PCT Filed: Dec. 5, 2012

(86) PCT No.: PCT/JP2012/081519
§ 371 (c)(1),
(2) Date: Jun. 1, 2015

(87) PCT Pub. No.: WO2014/087502
PCT Pub. Date: Jun. 12, 2014

(65) Prior Publication Data
US 2015/0327782 A1    Nov. 19, 2015

(51) Int. Cl.
*A61B 5/04* (2006.01)
*A61B 5/026* (2006.01)
*A61B 5/00* (2006.01)

(52) U.S. Cl.
CPC .......... *A61B 5/0261* (2013.01); *A61B 5/026* (2013.01); *A61B 5/6866* (2013.01); *A61B 5/74* (2013.01);
(Continued)

(58) Field of Classification Search
USPC ........................................................ 600/479
See application file for complete search history.

(56) References Cited

U.S. PATENT DOCUMENTS 6,515,273 B2    2/2003    Al-Ali
9,237,856 B2    1/2016    Tateishi
(Continued)

FOREIGN PATENT DOCUMENTS

JP    3490433    1/2004
JP    4460566    5/2010
(Continued)

OTHER PUBLICATIONS

International Search Report PCT/JP2012/081519 dated Jan. 8, 2013.

*Primary Examiner* — Nicole F Johnson
(74) *Attorney, Agent, or Firm* — Young & Thompson

(57) ABSTRACT

A measuring apparatus (100, 200, 300, 400) is an optical measuring apparatus provided with a probe portion (20, 20a, 20b, 20c) and a main body portion (10, 10b, 10c), which are electrically connected to each other. The probe portion has: a light source (21, 26); a reference voltage generating device (24) configured to apply predetermined reference voltage to the main body portion; and a storing device (25) configured to store therein in advance current adjustment information, which is information for adjusting a drive current to be supplied to the light source. The main body portion has: a drive current supplying device (12, 12a, 12b) configured to supply the drive current to the light source, due to the applied reference voltage; and a controlling device (11) configured to control the drive current supplying device on the basis of the stored current adjustment information.

5 Claims, 11 Drawing Sheets

(52) U.S. Cl.
CPC ....... *A61B 5/742* (2013.01); *A61B 2560/0266* (2013.01); *A61B 2560/0443* (2013.01); *A61B 2562/225* (2013.01); *F04C 2270/041* (2013.01)

(56) References Cited

U.S. PATENT DOCUMENTS

| | | |
|---|---|---|
| 2001/0022338 A1 | 9/2001 | Yanagisawa |
| 2007/0212038 A1 | 9/2007 | Asai et al. |
| 2009/0275844 A1 | 11/2009 | Al-Ali |
| 2011/0118575 A1* | 5/2011 | Lloyd .................. A61B 5/0059 600/328 |
| 2011/0190641 A1 | 8/2011 | Tateishi et al. |

FOREIGN PATENT DOCUMENTS

| | | |
|---|---|---|
| WO | 01/58347 A1 | 8/2001 |
| WO | 2005099575 | 10/2005 |
| WO | 2006064635 | 6/2006 |
| WO | 2009/134724 A1 | 11/2009 |
| WO | 2010023744 | 3/2010 |
| WO | 2011/161799 A1 | 12/2011 |

* cited by examiner

| ADDRESS NO. | DATA CONTENT |
|---|---|
| 0 | MANAGEMENT SERIAL NO. |
| 1 | YEAR AND MONTH OF MANUFACTURE |
| 2 | ... |
| 3 | LASER DRIVE ADJUSTMENT |
| 4 | VARIABLE GAIN AMPLIFIER ADJUSTMENT |
| 5 | USAGE TIME |
| ... | ... |

MEASURING APPARATUS, PROBE PORTION, AND CONNECTING CABLE

TECHNICAL FIELD

The present invention relates to an optical measuring apparatus configured to perform measurement by using light emitted from a light source such as, for example, a semiconductor laser, a probe portion that constitutes the measuring apparatus, and a connecting cable.

BACKGROUND ART

As this type of apparatus, for example, there is proposed an optical sensor having a light emitting element and a light receiving element, which are mounted on an insulated substrate, the optical sensor being provided with a cap for the light receiving element, the cap covering only the light receiving element and having an entrance window and a light polarizing surface (refer to Patent Literature 1). Alternatively, there is proposed a biological information monitoring system provided with a laser blood flowmeter configured to measure a blood flow on the basis of scattered light caused by scattering of laser light in a biological tissue (refer to Patent Literature 2).

CITATION LIST

Patent Literature

Patent Literature 1: Japanese Patent No. 4460566
Patent Literature 2: Japanese Patent No. 3490433

SUMMARY OF INVENTION

Technical Problem

According to the aforementioned background art, however, if there is a failure in a member on which the light source such as, for example, a semiconductor laser is mounted, replacement of the member or the like requires a relatively long period of time, and for example, production, work, and the like are likely delayed, which is technically problematic.

In view of the aforementioned technical problems, it is therefore an object of the present invention to provide a measuring apparatus, a probe portion, and a connecting cable, which allow a member including the light source to be replaced, relatively easily and in a short time.

Solution to Problem

The above object of the present invention can be achieved by a measuring apparatus of an optical type is provided with a probe portion and a main body portion, which are electrically connected to each other, said probe portion having; a light source; a reference voltage generating device configured to apply predetermined reference voltage to said main body portion; and a storing device configured to store therein in advance current adjustment information, which is information for adjusting a drive current to be supplied to the light source, said main body portion having; a drive current supplying device configured to supply the drive current to the light source, due to the applied reference voltage; and a controlling device configured to control the drive current supplying device in such a manner that the drive current has a drive current value to be supplied to the light source, on the basis of the stored current adjustment information.

The above object of the present invention can be achieved by a measuring apparatus of an optical type is provided with a probe portion and a main body portion, which are electrically connected to each other, said probe portion having; a light source; a reference voltage generating device configured to apply predetermined reference voltage to said main body portion; a storing device configured to store therein in advance current adjustment information, which is information for adjusting a drive current to be supplied to the light source; and a light receiving device configured to receive scattered light from an object of light emitted from the light source and to output a light receiving signal, said main body portion having: a drive current supplying device configured to supply the drive current to the light source, due to the applied reference voltage; a controlling device configured to control the drive current supplying device in such a manner that the drive current has a drive current value to be supplied to the light source, on the basis of the stored current adjustment information; and an arithmetic operating device configured to arithmetically operate a state quantity associated with the object, on the basis of the outputted light receiving signal.

The above object of the present invention can be achieved by a probe portion, which is electrically connected to a main body portion of a measuring apparatus of an optical type and to which a drive current from the main body portion is supplied, said probe portion is provided with: a light source configured to emit light, due to the drive current; a reference voltage generating device configured to apply predetermined reference voltage for generating the drive current, to the main body portion; and a storing device configured to store therein in advance current adjustment information, which is information for adjusting the drive current, in the main body portion.

The above object of the present invention can be achieved by a connecting cable configured to electrically connect a probe portion and a main body to each other, in a measuring apparatus of an optical type is provided with: the probe portion having a light source; and the main body portion having a drive current supplying device configured to supply a drive current to the light source and a controlling device configured to control the drive current supplying device, said connecting cable comprising a connector configured to be attached to or be detached from the probe portion or the main body portion, the connector having: a reference voltage generating device configured to apply predetermined reference voltage for allowing the drive current supplying device to generate the drive current, to the main body portion; and a storing device configured to store therein in advance current adjustment information, which is information for allowing the controlling device to adjust the drive current.

The operation and other advantages of the present invention will become more apparent from embodiments and examples explained below.

Figure 1:
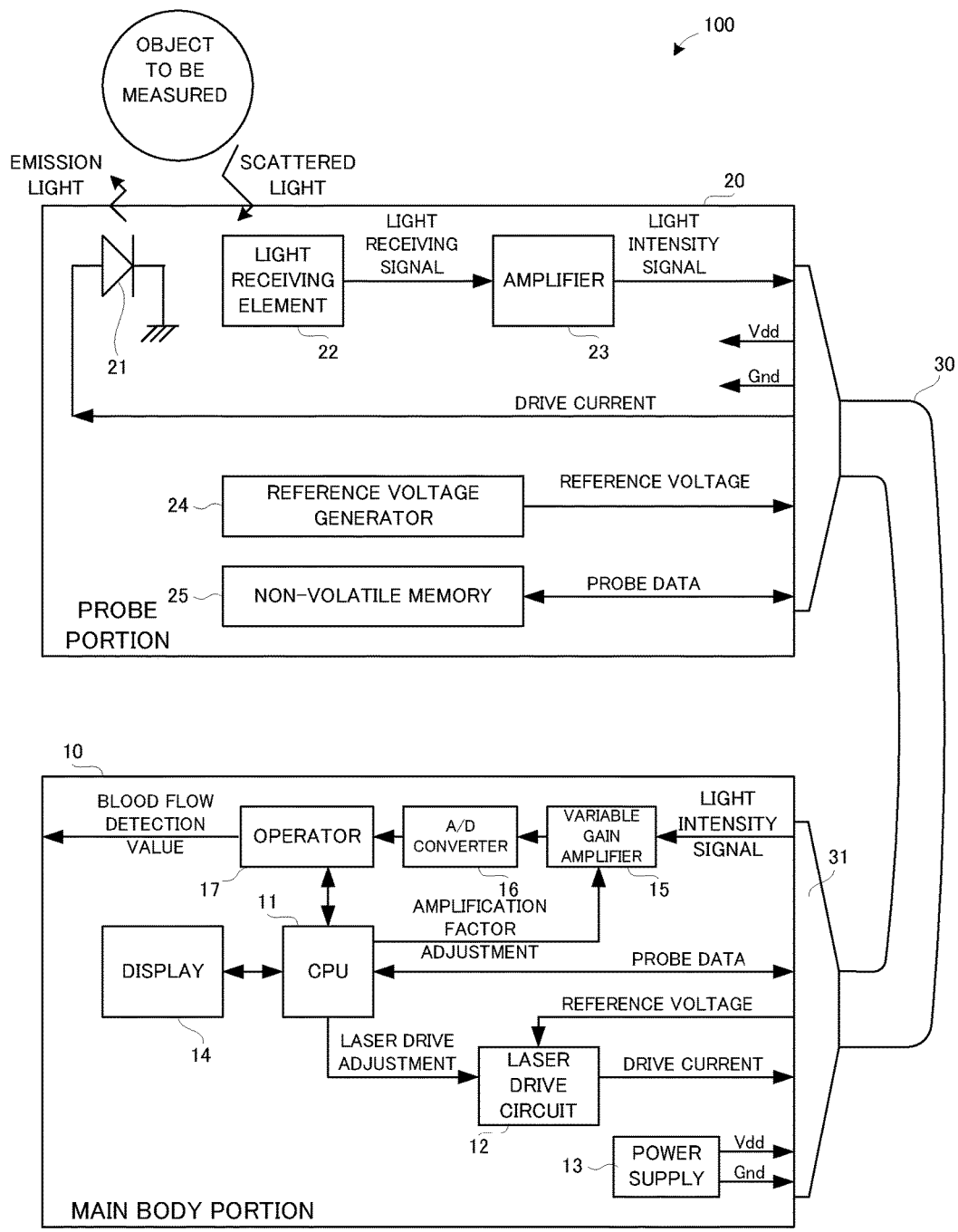
FIG. 1 is a block diagram illustrating a configuration of a measuring apparatus according to a first example.

DESCRIPTION OF EMBODIMENTS (Embodiments of Measuring Apparatus)

A first measuring apparatus according to an embodiment is a measuring apparatus of an optical type is provided with a probe portion and a main body portion, which are electrically connected to each other, said probe portion having: a light source; a reference voltage generating device configured to apply predetermined reference voltage to said main body portion; and a storing device configured to store therein in advance current adjustment information, which is information for adjusting a drive current to be supplied to the light source, said main body portion having: a drive current supplying device configured to supply the drive current to the light source, due to the applied reference voltage; and a controlling device configured to control the drive current supplying device in such a manner that the drive current has a drive current value to be supplied to the light source, on the basis of the stored current adjustment information.

According to the first measuring apparatus in the embodiment, the measuring apparatus is the optical measuring apparatus. The measuring apparatus is provided with the main body portion and the probe portion, which are electrically connected to each other. The main body portion is provided with the drive current supplying device and the controlling device. The probe portion is provided with the light source, the reference voltage generating device, and the storing device.

In operation of the measuring apparatus, the predetermined reference voltage is applied to the main body portion by the reference voltage generating device of the probe portion. The predetermined reference voltage is supplied to the drive current supplying device of the main body portion. The controlling device of the main body portion obtains the current adjustment information stored in advance in the storing device of the probe portion. The controlling device then controls the drive current supplying device in such a manner that the drive current has the drive current value to be supplied to the light source of the probe portion, on the basis of the obtained current adjustment information.

As a result, an appropriate drive current is supplied to the light source of the probe portion from the drive current supplying device. The light source such as, for example, a semiconductor laser and a light emitting diode emits light in response to the supply of the drive current. The measuring apparatus performs measurement by receiving scattered light caused by the emitted light. Since various known aspects can be applied to the measurement, an explanation of the measurement is omitted herein.

By the way, if the probe portion is replaced, for example, due to a lifetime of the light source or the like, it is necessary to adjust the light source upon replacement, so as to emit light with appropriate power. It is hard for a user to adjust the light source, and it is often necessary to make a request of an external organization such as, for example, a service man. Then, due to the replacement of the probe portion, work and inspection or examination are likely delayed for a relatively long period of time.

Thus, in the embodiment, the storing device stores therein in advance the current adjustment information for adjusting the drive current to be supplied to the light source. Then, the drive current supplying device is controlled by the controlling device in such a manner that the drive current has the drive current value to be supplied to the light source or the probe portion, on the basis of the current adjustment information. Thus, the adjustment of the light source (i.e. the adjustment of the drive current to be supplied to the light source) is automatically performed if the user only replaces the probe portion. The probe portion thus can be replaced, relatively easily and in a short time.

A second measuring apparatus according to an embodiment is a measuring apparatus of an optical type is provided with a probe portion and a main body portion, which are electrically connected to each other, said probe portion having: a light source; a reference voltage generating device configured to apply predetermined reference voltage to said main body portion; a storing device configured to store therein in advance current adjustment information, which is information for adjusting a drive current to be supplied to the light source; and a light receiving device configured to receive scattered light from an object of light emitted from the light source and to output a light receiving signal, said main body portion having: a drive current supplying device configured to supply the drive current to the light source, due to the applied reference voltage; a controlling device configured to control the drive current supplying device in such a manner that the drive current has a drive current value to be supplied to the light source, on the basis of the stored current adjustment information; and an arithmetic operating device configured to arithmetically operate a state quantity associated with the object, on the basis of the outputted light receiving signal.

According to the second measuring apparatus in the embodiment, the measuring apparatus is the optical measuring apparatus. The measuring apparatus is provided with the main body portion and the probe portion, which are electrically connected to each other. The main body portion is provided with the drive current supplying device, the controlling device, and the arithmetic operating device. The probe portion is provided with the light source, the light receiving device, the reference voltage generating device, and the storing device.

In operation of the measuring apparatus, the light receiving device of the probe portion receives the scattered light from the object of the light emitted from the light source, and outputs the light receiving signal. The arithmetic operating device of the main body arithmetically operates the state quantity associated with the object, on the basis of the outputted light receiving signal.

Even in the second measuring device, the storing device stores therein the current adjustment information for adjusting the drive current to be supplied to the light source. Therefore, as in the aforementioned first measuring apparatus, the probe portion can be replaced, relatively easily and in a short time.

In one aspect of the first and second measuring apparatuses, the storing device further stores therein usage time information, which is information indicating a usage time of said probe portion.

According to this aspect, the usage time information is stored in the storing device, and it is thus possible to appropriately manage the usage time of the probe portion. It is therefore possible to relatively easily know, for example, replacement timing of the probe portion or the like.

In this aspect, the controlling device updates the usage time information, according to an operating time of said measuring apparatus.

By virtue of such a configuration, the usage time information can be updated, relatively easily, which is extremely useful in practice.

In this aspect, said main body portion further has a notifying device configured to notify a user of said measuring device if the usage time indicated by the stored usage time information is greater than a predetermined value.

By virtue of such a configuration, the user can relatively easily know, for example, the replacement timing of the probe portion or the like, which is extremely useful in practice.

Here, the "predetermined value" according to the embodiment is a value for determining whether or not to notify the user, and is set as a fixed value in advance, or a variable value according to some physical quantity or parameter. Such a "predetermined value" may be set as a usage time in which degree of deterioration of the light source is greater than an allowable range, for example, on the basis of a relation between the usage time of the light source and the degree of the deterioration of the light source, wherein the relation is obtained by experiments, experiences, or simulations.

In another aspect of the second measuring apparatus, said main body portion further has an amplifying device configured to amplify the outputted light receiving signal in a such a manner that an amplification factor is variable, and the storing device further stores therein amplification factor adjustment information, which is information for adjusting the amplification factor associated with the amplifying device.

According to this aspect, for example, the controlling device of the main body portion can easily adjust the amplifying device with reference to the amplification factor adjustment information.

According to this aspect, said controlling device controls the amplifying device on the basis of the stored amplification factor adjustment information.

By virtue of such a configuration, the amplification factor of the amplifying device can be adjusted, relatively easily, which is extremely useful in practice.

In another aspect of the first and second measuring apparatuses, said measuring apparatus is a blood flow detecting apparatus.

According to this aspect, a blood flow can be detected, relatively easily.

(Embodiment of Probe Portion)

A probe portion according to an embodiment is a probe portion, which is electrically connected to a main body portion of a measuring apparatus of an optical type and to which a drive current from the main body portion is supplied, said probe portion is provided with: a light source configured to emit light, due to the drive current; a reference voltage generating device configured to apply predetermined reference voltage for generating the drive current, to the main body portion; and a storing device configured to store therein in advance current adjustment information, which is information for adjusting the drive current, in the main body portion.

According to the probe portion in the embodiment, as in the first and second measuring apparatuses according to the aforementioned embodiments, the probe portion can be replaced, relatively easily and in a short time.

(Embodiment of Connecting Cable)

A connecting cable according to an embodiment is a connecting cable configured to electrically connect a probe portion and a main body to each other, in a measuring apparatus of an optical type is provided with: the probe portion having a light source; and the main body portion having a drive current supplying device configured to supply a drive current to the light source and a controlling device configured to control the drive current supplying device, said connecting cable comprising a connector configured to be attached to or be detached from the probe portion or the main body portion, the connector having: a reference voltage generating device configured to apply predetermined reference voltage for allowing the drive current supplying device to generate the drive current, to the main body portion; and a storing device configured to store therein in advance current adjustment information, which is information for allowing the controlling device to adjust the drive current.

According to the connecting cable in the embodiment, as in the first and second measuring apparatuses according to the aforementioned embodiments, the probe portion can be replaced, relatively easily and in a short time.

EXAMPLES

First Example

A first example according to the measuring apparatus of the present invention will be explained on the basis of the drawings.

Firstly, a configuration of the measuring apparatus according to the example will be explained with reference to FIG. 1. FIG. 1 is a block diagram illustrating the configuration of the measuring apparatus according to the first example.

In FIG. 1, a measuring apparatus 100 is provided with a main body portion 10, a probe portion 20, and a connecting cable 30 configured to electrically connect the main body portion 10 and the probe portion 20 to each other.

The main body portion 10 is provided with a central processing unit (CPU) 11, a laser drive circuit 12, a power supply 13, a display 14, a variable gain amplifier 15, an analog to digital (A/D) converter 16, and an operator 17.

The probe portion 20 is provided with a light source 21 such as, for example, a semiconductor laser, a light receiving element 22, an amplifier 23, a reference voltage generator 24, and a non-volatile memory 25 configured to store therein predetermined probe data.

The connecting cable 30 is formed integrally with the probe portion. At one end of the connecting cable 30, there is provided a connector 31 formed detachably from the main body portion 10.

The "CPU 11", the "laser drive circuit 12", the "display 14", the "variable gain amplifier 15", the "operator 17", the "light receiving element 22", the "reference voltage generator 24", and the "non-volatile memory 25" according to the example are, respectively, one example of the "controlling device", the "drive current supplying device", the "notifying device", the "amplifying device", the "arithmetic operating device", the "light receiving device", the "reference voltage generating device", and the "storing device" according to the present invention.

In operation of the measuring apparatus 100, a power supply potential Vdd associated with the power supply 13 of the main body portion 10 is supplied to the probe portion 20 via the connecting cable 30. In the probe portion 20, the power supply potential Vdd is supplied to, for example, the reference voltage generator 24. In the reference voltage generator 24, reference voltage is generated according to the power supply potential Vdd. The generated reference voltage is applied to the laser drive circuit 12 of the main body portion 10 via the connecting cable 30.

Figure 2:
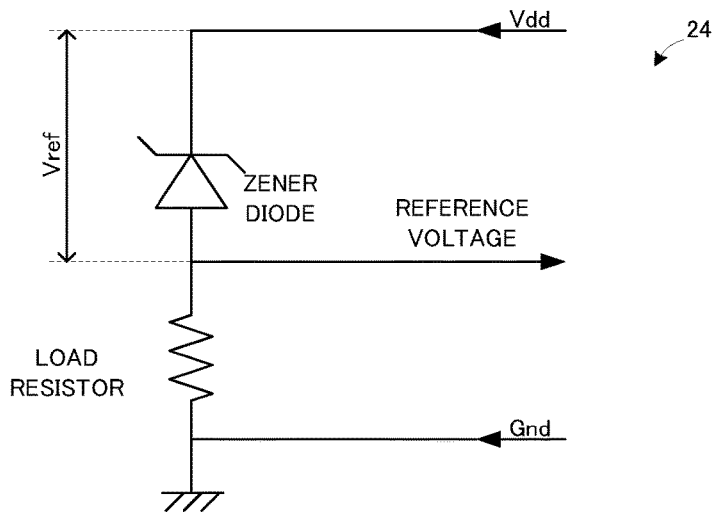
FIG. 2 is a diagram illustrating one example of an electric circuit associated with a reference voltage generator according to the first example.

Now, the reference voltage generator 24 will be explained with reference to FIG. 2. FIG. 2 is a diagram illustrating one example of an electric circuit associated with the reference voltage generator according to the first example.

In FIG. 2, the reference voltage generator 24 is provided with a Zener diode. The power supply potential Vdd is supplied to a cathode of the Zener diode. An anode of the Zener diode is connected to a ground (Gnd) wire via a load resistor.

Voltage between the cathode and the anode of the Zener diode is Zener voltage Vref defined by characteristics of the Zener diode. Therefore, a potential of the anode of the Zener diode is "(Power supply potential Vdd) −(Zener voltage Vref)". The potential of the anode is applied, as the reference voltage, to the laser drive circuit 12 of the main body portion 10 via the connecting cable 30.

Back in FIG. 1 again, the CPU 11 of the main body portion 10 obtains the probe data (refer to FIG. 6) stored in advance in the non-volatile memory 25 of the probe portion 20, via the connecting cable 30. The CPU 11 controls the laser drive circuit 12 in such a manner that a predetermined drive current is outputted, on the basis of a laser drive adjustment value included in the obtained probe data.

Figure 3:
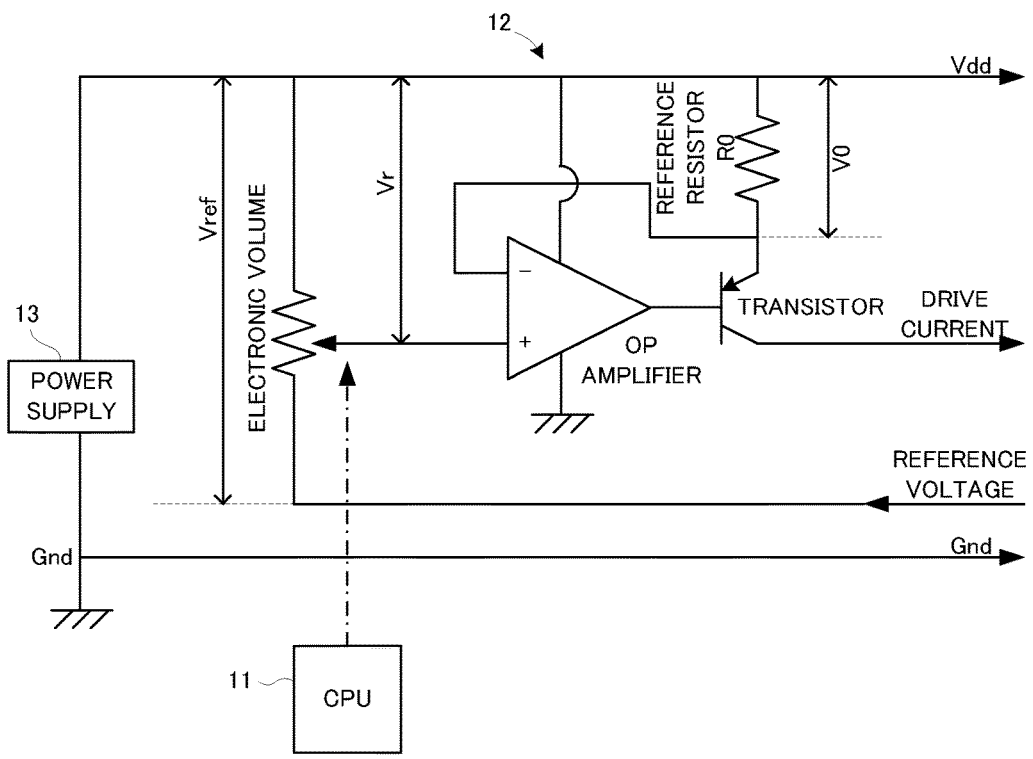
FIG. 3 is a diagram illustrating one example of an electric circuit associated with a laser drive circuit according to the first example.

Now, the laser drive circuit 12 will be explained with reference to FIG. 3. FIG. 3 is a diagram illustrating one example of an electric circuit associated with the laser drive circuit according to the first example.

In FIG. 3, the laser drive circuit 12 is provided with an electronic volume for generating adjustment voltage Vr for adjusting the drive current, a reference resistor R0, an operational (OP) amplifier for matching the adjustment voltage Vr with voltage drop V0 by the reference resistor R0, and a transistor for outputting the drive current.

The electronic volume has the power supply potential Vdd associated with the power supply 13 at one end, and the electronic volume has the reference voltage (i.e. "(Power supply potential Vdd)−(Zener voltage Vref)") at the other end. Therefore, voltage between the both ends of the electronic volume is Vref. The electronic volume has, for example, a resolution of 6 bits. Voltage between a sweep terminal of the electronic volume and the power supply potential Vdd (i.e. the adjustment voltage Vr) is expressed by the following equation (1).

$$\text{Adjustment Voltage } Vr = n \cdot Vref/63 \tag{1}$$

wherein, "n" is the laser drive adjustment value, which is information for adjusting the drive current to be supplied to the light source 21, and a value thereof is an integer of 0 to 63. The laser drive adjustment value, as described above, is included in the obtained probe data, and is specified by the CPU 11. The "laser drive adjustment value" according to the example is one example of the "current adjustment information" according to the present invention.

As illustrated in FIG. 3, the sweep terminal of the electronic volume is connected to a +terminal of the OP amplifier. An imaginary short is established by an action of negative feedback of the OP amplifier, and the +terminal and −terminal of the OP amplifier have the same potential; namely, the following equation applies.

$$(\text{Adjustment Potential } Vr) = (\text{Voltage Drop } V0 \text{ by Reference Resistor } R0) \tag{2}$$

Here, a collector current of the transistor is greater than a base current, for example, by about two digits. Moreover, impedance of the −terminal of the OP amplifier is greater than the reference resistor R0, for example, by several digits. Thus, if the base current and an input current to the OP amplifier are ignored, it can be said that a current flowing through the reference resistor R0 is equal to a drive current If, which is the collector current; namely, the following equation applies.

$$\text{Drive Current } If = V0/R0 \tag{3}$$

From the aforementioned equations (1), (2), and (3), the following equation applies.

$$\text{Drive Current } If = Vr/R0 = n \cdot Vref/(63 \ast R0) \tag{4}$$

As is clear from the aforementioned equation (4), if the reference resistor R0 is constant, the drive current If is proportional to "n·Vref". Thus, the drive current If can be controlled by the CPU 11 specifying the laser drive adjustment value n.

Now, one example of a method of determining the reference resistor R0 will be explained. Firstly, power of emission light required for the measuring apparatus 100 (or "target optical power" in FIG. 5 described later) is determined according to an object to be measured by the measuring apparatus 100. Then, the drive current If that satisfies the power of the emission light required is determined on the basis of a representative value of characteristics associated with an element used as the light source 21 of the measuring apparatus 100 (e.g. I-P properties or the like in the case of a semiconductor laser). Moreover, the Zener voltage Vref (i.e. Zener diode) that is smaller than the power supply potential Vdd is selected according to the power supply potential Vdd.

Specifically, for example, it is assumed that the power of the emission light required is 10 mW, that the drive current If that satisfies the power of the emission light required is 25 mA, that the power supply potential Vdd is 10V, and that the Zener voltage is 5 V.

The reference resistor R0 is determined from the drive current If and the Zener voltage Vref, which are determined or selected in the above manner, and the aforementioned equation (4). The laser drive adjustment value n may be set to, for example, 32. As described above, if the drive current If is 25 mA and the Zener voltage is 5 V, the reference resistor R0 is 100 Ω.

In practice, the measuring apparatus 100 may be designed while the element that constitutes the light source 21, the power supply 13, and the like are appropriately selected, for example, in such a manner that the Zener voltage Vref, the reference resistor R0, and the like have appropriate values.

Back in FIG. 1 again, the drive current If outputted from the laser drive circuit 12 is supplied to the light source 21 of the probe portion 20 via the connecting cable 30. As a result, light is emitted from the light source 21 to the object to be measured (e.g. blood flowing through capillary vessels of a human body, etc.). The light receiving element 22 receives scattered light caused by the emitted light (or the emission light) and outputs a light receiving signal.

If the object to be measured is blood, the emission light is scattered by red blood cells (or moving objects) in the blood. At this time, due to the laser Doppler effect, frequency of the light varies depending on a moving speed of the red blood cells. Moreover, the emission light is also scattered by non-moving objects such as skin tissues. The scattered light by the red blood cells and the scattered light by the non-moving objects interfere with each other and generate an optical beat signal. The light receiving element 22 detects the optical beat signal and outputs it as the light receiving signal.

The amplifier 23 of the probe portion 20 amplifies the light receiving signal and outputs a light intensity signal, which is the amplified light receiving signal. The variable gain amplifier 15 of the main body portion 10 amplifies the light intensity signal in such a manner that the light intensity signal can be appropriately A/D converted on the subsequent A/D converter 16.

Figure 4:
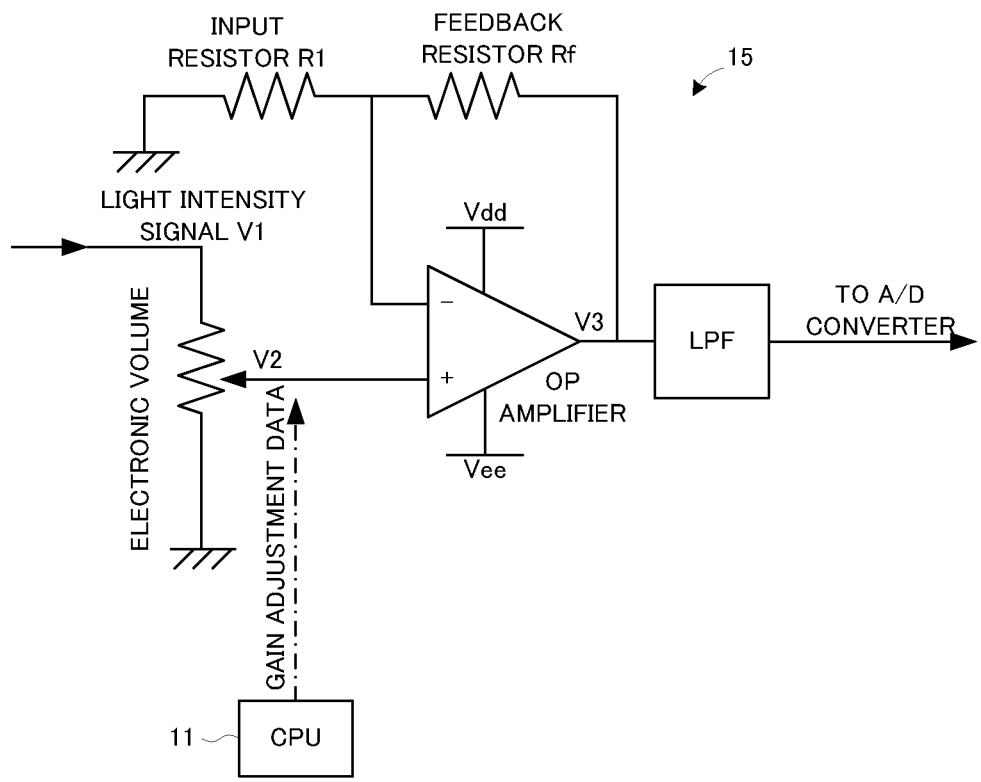
FIG. 4 is a diagram illustrating one example of an electric circuit associated with a variable gain amplifier according to the first example.

Now, the variable gain amplifier 15 will be explained with reference to FIG. 4. FIG. 4 is a diagram illustrating one example of an electric circuit associated with the variable gain amplifier according to the first example.

In FIG. 4, a light intensity signal V1 outputted from the probe portion 20 is inputted to one end of an electronic volume. The electronic volume is set to have reference potential such as, for example, ground potential at the other end. A sweep terminal of the electronic volume is connected to a non-inverting input terminal of an OP amplifier. One end of an input resistor R1 and one end of a feedback resistor Rf are connected to the inverting input terminal of the OP amplifier. The input resistor R1 is set to have reference potential such as, for example, ground potential at the other end. The other end of the feedback resistor Rf is connected to an output terminal of the OP amplifier.

The electronic volume has, for example, a resolution of 6 bits. The light intensity signal V1 outputted from the probe portion 20 is temporarily attenuated according to a set value of the electronic volume, and is outputted as a signal V2 to the sweep terminal. The signal V2 is amplified by the OP amplifier and is outputted as a signal V3.

The signal V2 is expressed by the following equation (5).

$$V2=(G1/63)V1 \quad (5)$$

wherein, "G1" is the set value of the electronic volume, and a value thereof is, for example, an integer of 0 to 63.

Transfer characteristics from the non-inverting input terminal of the OP amplifier to the output are expressed by the following equation (6).

$$V3/V2=1+Rf/R1 \quad (6)$$

From the equations (5) and (6), $$V3=(1+Rf/F1)V2=(1+Rf/R1)(G1/63)V1 \quad (7)$$

In other words, the light intensity signal V1 is amplified by the variable gain amplifier 15 in accordance with the equation (7).

If "Rf/R1" is constant, the light intensity signal V1 is amplified in proportion to the set value G1. If, for example, a metal film resistor or the like is used as the feedback resistor Rf and the input resistor R1, it is relatively easy to keep "Rf/R1" constant. Although the resistors have temperature properties, the temperature properties of a resistance ratio can be ignored if the resistors are closely arranged on the same substrate.

Moreover, a maximum resistance value of the electronic volume has relatively wide variation in products; however, a ratio among the sweep terminal, inter-terminal resistance (or sweep resistance value), and the maximum resistance value is almost constant regardless of products, and the product variation of the maximum resistance value can be ignored.

Thus, variation in amplification factor indicated by the aforementioned equation (7) can be ignored. As a result, the light intensity signal V1 is amplified with an accurate amplification factor in accordance with the set value G1, and is outputted as the signal V3.

Back in FIG. 1 again, the A/D converter 16 A/D-converts the amplified light intensity signal and outputs quantized data. The operator 17 performs arithmetic operation based on frequency analysis such as, for example, Fast Fourier Transform (FFT), on the outputted quantified data. Since various known aspects can be applied to a method of obtaining a blood flow detection value, which is one example of the arithmetic operation performed on the operator 17, an explanation of the details will be omitted.

Figures 5, 6:
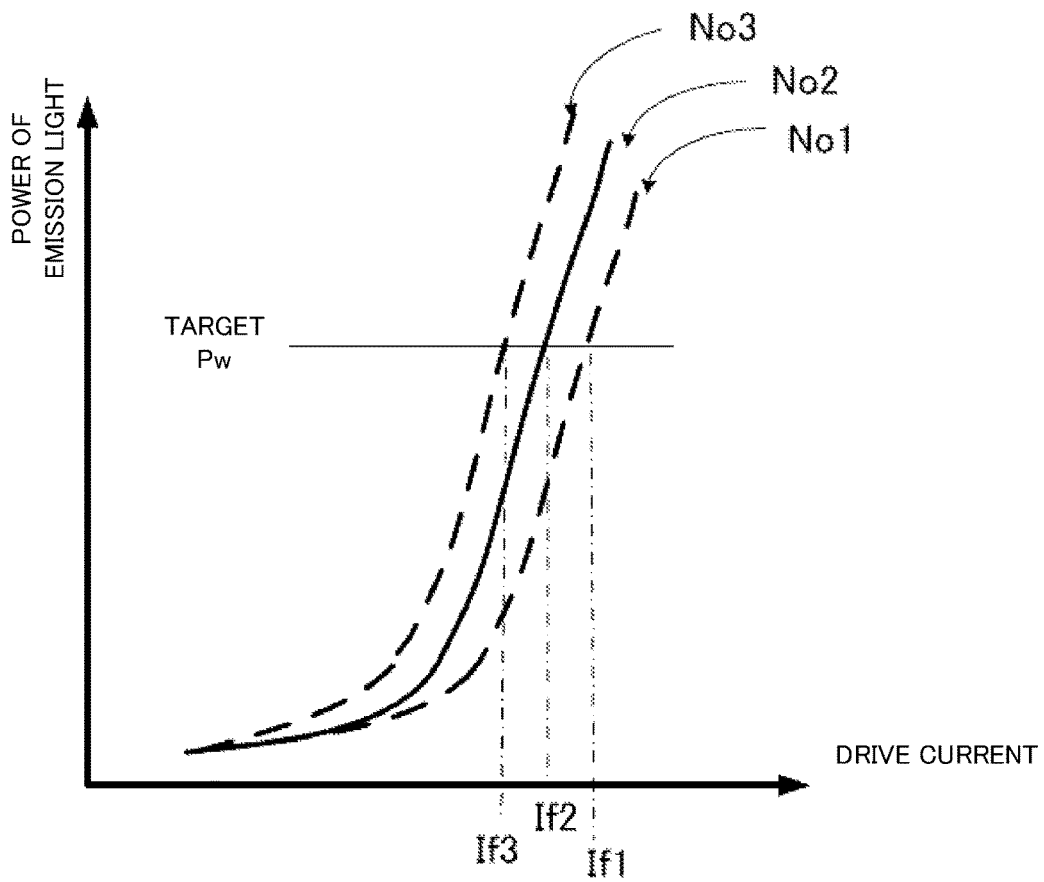
FIG. 5 is a characteristic diagram illustrating one example of I—P properties of a semiconductor laser.
FIG. 6 is a diagram illustrating one example of probe data stored in a non-volatile memory according to the first example.

Next, characteristics of a semiconductor laser that can be used as the light source 21 of the probe portion 20 will be explained with reference to FIG. 5. FIG. 5 is a characteristic diagram illustrating one example of I—P properties of the semiconductor laser.

A semiconductor laser having properties corresponding to a dashed line with a reference numeral "No1" outputs emission light with target optical power Pw if a drive current If1 is supplied. A semiconductor laser having properties corresponding to a solid line with a reference numeral "No2" outputs emission light with target optical power Pw if a drive current If2, which is smaller than the drive current If1, is supplied. A semiconductor laser having properties corresponding to a dashed line with a reference numeral "No3" outputs emission light with target optical power Pw if a drive current If3, which is smaller than the drive current If2, is supplied.

As described above, there is more or less variation among individual semiconductor lasers even if the same standard is used. In other words, unless the drive current according to the characteristics of the semiconductor laser is supplied, the emission light with appropriate optical power cannot be obtained.

If the power of the emission light is lower than the target optical power Pw, power of the scattered light received by the light receiving element 22 also decreases, and thus, a signal to noise ratio (S/N) of the outputted light receiving signal (and light intensity signal) decreases. On the other hand, if the power of the emission light is higher than the target optical power Pw, there is a possibility of troubles during the measurement.

Thus, in the conventional technology, if there is a failure in the probe portion of the measuring apparatus, it is required to perform the same power adjustment of the emission light as that upon product shipment, for example, by a service man when the probe portion is replaced. In other words, it is necessary to request an external organization to replace the probe portion, and the replacement of the probe portion takes a time in many cases. Then, there is a possibility that work or the like is significantly delayed due to the failure of the probe portion. The same can also apply to another element that can be used as the light source 21 such as, for example, a light-emitting diode.

In the measuring apparatus 100 according to the example, however, the probe data including the laser drive adjustment value is stored in advance in the non-volatile memory 25, as described above. Thus, even if the probe portion 20 of the measuring apparatus 10 is replaced, the CPU 11 of the main body portion 10 controls the laser drive circuit 12 on the basis of the probe data stored in advance in the non-volatile memory 25 of the replaced probe portion 20, by which an appropriate drive current can be supplied to the light source 21. In other words, it is no longer necessary to adjust the light source 21, for example, by the service man or the like when the probe portion 20 is replaced.

As a result, a user of the measuring apparatus 100 can replace the probe portion 20, relatively easily and in a short time. In addition, only the replacement of the probe portion 20 is required. It is thus possible to significantly save costs in comparison with a case where the measuring apparatus 100 is replaced by a new one, which is extremely useful in practice. Moreover, the probe portion 20 can be replaced in a relatively short time. It is thus not necessary to prepare for a spare measuring apparatus, or it is possible to reduce the number of the spare measuring apparatuses.

Next, the probe data stored in the non-volatile memory 25 will be explained with reference to FIG. 6. FIG. 6 is a diagram illustrating one example of the probe data stored in the non-volatile memory according to the first example.

As illustrated in FIG. 6, the probe data includes, for example, "management serial number" and "year and month of manufacture" associated with the probe portion 20, the "laser drive adjustment value", a "variable gain amplifier adjustment value", and a "usage time" associated with the probe portion 20 (or the light source 21 herein), and the like.

The "variable gain amplifier adjustment value" is one example of the "amplification factor adjustment information" according to the present invention, and is information for adjusting the amplification factor associated with the variable gain amplifier 15 of the main body portion 10.

(Process Upon Shipment)

Next, a method of setting the laser drive adjustment value upon shipment will be explained with reference to a flowchart in FIG. 7.

Figure 7:
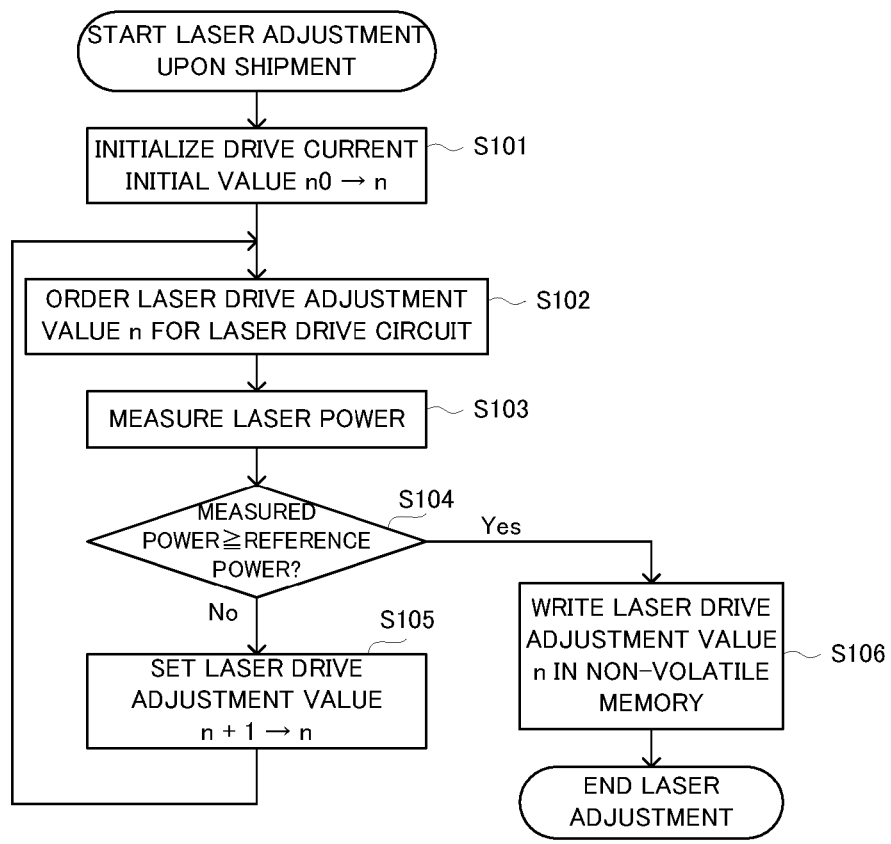
FIG. 7 is a flowchart illustrating a laser adjustment process upon shipment.

In FIG. 7, if a laser power adjustment process is required for the CPU 11 of the main body portion 10 by external input, the CPU 11 stores an initial value (e.g. n0=0) in a register within the CPU 11, as the laser drive adjustment value n, in order to initialize the drive current to be supplied to the light source 21 of the probe portion 20 (step S101).

The CPU 11 then orders the laser drive adjustment value n for the electronic volume of the laser drive circuit 12 (refer to FIG. 3) (step S102). As a result, the drive current is supplied to the light source 21 of the probe portion 20 from the laser drive circuit 12.

Then, laser power of laser light emitted from the light source 21 is measured by an optical power measuring instrument (not illustrated) located in the exterior, and a measurement result is transmitted to the CPU 11 of the main body portion 10 (step S103). The CPU 11 then determines whether or not the measured laser power is greater than or equal to reference power, which is a target (step S104).

If the measured laser power is greater than or equal to the reference power (the step S104: Yes), the CPU 11 writes the present laser drive adjustment value n in the non-volatile memory 25 of the probe portion 20 (step S106), and ends the process.

On the other hand, if the measured laser power is less than the reference power (the step S104: No), the CPU 11 resets the laser drive adjustment value n (step S105), and performs the process in the step S102 again.

Now, a reason why the probe portion 20 is provided with the reference voltage generator 24 will be explained.

The laser drive circuit 12, as described above, generates the drive current by the application of the reference voltage (e.g. refer to FIG. 1 and FIG. 3). The reference voltage is determined by the Zener diode (refer to FIG. 2) of the reference voltage generator 24.

It has been found by the study of the present inventor that the Zener diode has about plus/minus several percent of individual variation. If the probe portion 20 is replaced in a case where the main body portion 10 is provided with the reference voltage generator 24, the reference voltage is likely changed from reference voltage when the laser drive adjustment value is set, due to the individual variation of the Zener diode. Then, even if the laser drive adjustment value is set upon shipment, as described above, there is a possibility that the appropriate drive current is not supplied, depending on the main body portion 10 to which the probe portion 20 is electrically connected.

In the example, however, the reference voltage generator 24 is provided for the probe portion 20, as described above. Therefore, even if the probe portion 20 is replaced, the reference voltage can be kept the same as the reference voltage when the laser drive adjustment value is set. In other words, because the probe portion 20 is provided with the reference voltage generator 24, it is possible to suppress variation in the drive current caused by the individual variation of the Zener diode, which constitutes the reference voltage generator 24.

Next, a method of setting the variable gain amplifier adjustment value upon shipment will be explained with reference to a flowchart in FIG. 8.

Firstly, necessity of the variable gain amplifier adjustment value will be explained. Due to individual variation of the probe portion 20 caused by, for example, sensitiveness variation of the light receiving element 22, mounting position deviation of the light receiving element 22, position deviation of a lens (not illustrated), position deviation of the light source 21 or the like, the light intensity signal (refer to FIG. 1) from the probe portion 20 changes (e.g. amplitude fluctuation) even if the laser light emitted from the light source 21 has constant power.

If the light intensity signal is A/D converted without correcting the amplitude fluctuation of the light intensity signal, the following disadvantages possibly occur. If the light intensity signal has too small amplitude, an amplitude amount is insufficient for an input D range of the A/D converter 16, and thus, a quantization error may occur, and a large error may occur in the subsequent arithmetic operation. On the other hand, if the light intensity signal has too large amplitude, the amplitude amount exceeds the input D range of the A/D converter 16, and thus, the quantized data is saturated and the signal is distorted, and a large error may occur in the subsequent arithmetic operation.

Therefore, in order to correct variation in the light intensity signal caused by the individual variation of the probe portion 20, it is necessary to change the amplification factor of the variable gain amplifier 15 of the main body portion 10, in accordance with the probe portion 20. Particularly in the example, the variable gain amplifier adjustment value is stored in advance in the non-volatile memory 25 of the probe portion 20, by which the user can replace the probe portion 20, relatively easily.

Figure 8:
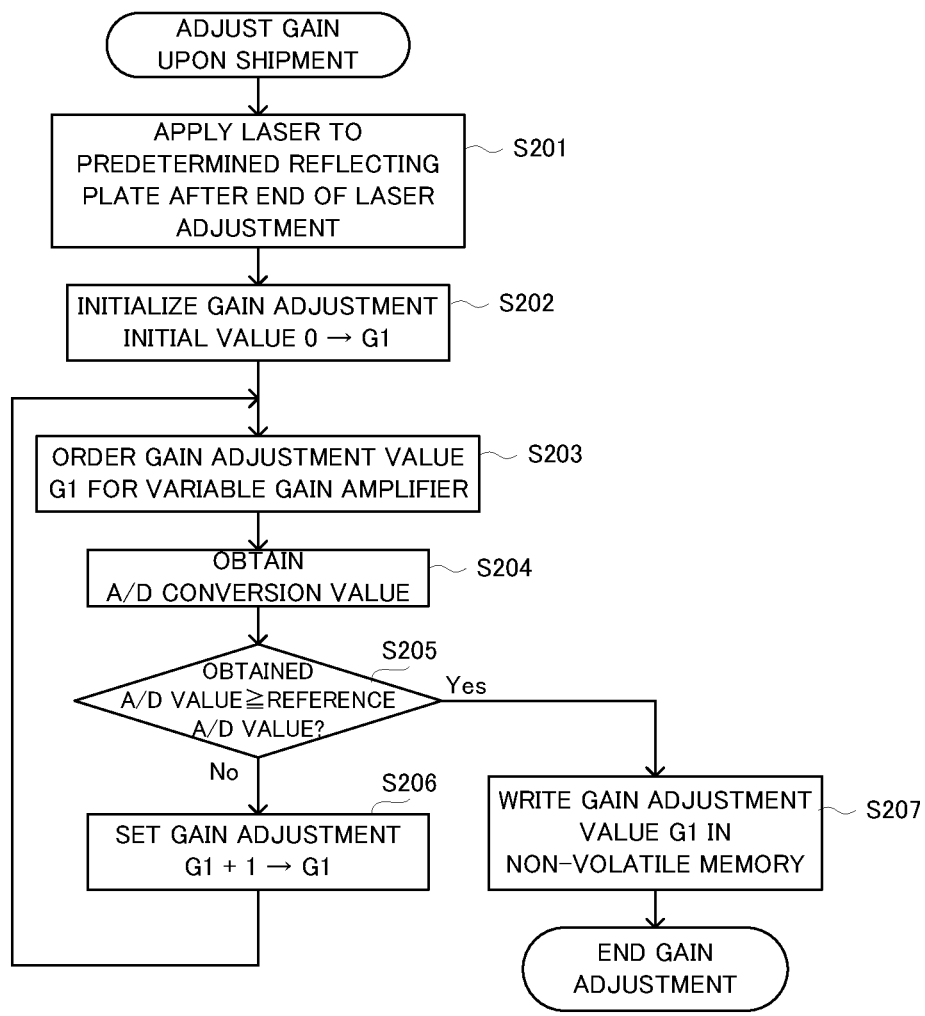
FIG. 8 is a flowchart illustrating a gain adjustment process upon shipment.

In FIG. 8, after the end of the process of setting the laser drive adjustment value upon shipment described above, the laser light is applied from the light source 21 to a reflecting plate (not illustrated) with a predetermined reflectivity, with appropriate optical arrangement maintained (step S201). The CPU 11 of the main body portion 10 then initializes the variable gain amplifier adjustment value and stores it in the register within the CPU 11 (step S202).

The CPU 11 then orders the variable gain amplifier adjustment value G1 for the electronic volume of the variable gain amplifier 15 (refer to FIG. 4) (step S203). The CPU 11 then obtains an A/D conversion value associated with the A/D converter 16 (step S204). The CPU 11 then determines whether or not the obtained A/D conversion value is greater than or equal to a reference A/D value, which is a target (step S205).

Here, the "reference A/D value" may be set, for example, as an A/D conversion value when a typical light intensity signal outputted from the probe portion 20 is inputted to the A/D converter 16 in the case of reception of the scattered light when the laser light with specified laser power is applied to the reflecting plate with the predetermined reflectivity. In this case, a center value (e.g. 32) is set as the variable gain amplifier adjustment value G1.

If it is determined that the obtained A/D conversion value is greater than or equal to the reference A/D value (the step S205: Yes), the CPU 11 writes the present variable gain amplifier adjustment value G1 in the non-volatile memory 25 of the probe portion 20 (step S207), and ends the process.

On the other hand, if it is determined that the obtained A/D conversion value is less than the reference A/D value (the step S205: No), the CPU 11 resets the variable gain amplifier adjustment value G1 (step S206), and performs the process in the step S203 again.

As described above, the light intensity signal is amplified with an accurate amplification factor in accordance with the set value G1, and is outputted as the signal V3 (refer to FIG. 4). Thus, if the variable gain amplifier adjustment value G1 stored in the non-volatile memory 25 is referred to, an amplitude level suitable for the input D range of the A/D converter 16 is maintained even if the probe portion 20 is replaced. If the signal V3 with appropriate amplitude is inputted to the A/D converter 16, it is possible to suppress an increase in quantization error when the amplitude is low, and it is also possible to suppress the signal distortion due to the saturation when the amplitude is high.

(Process Upon Measurement)

Next, a process upon the measurement of the measuring apparatus 100 will be explained with reference to flowcharts in FIG. 9 to FIG. 11.

Figure 9:
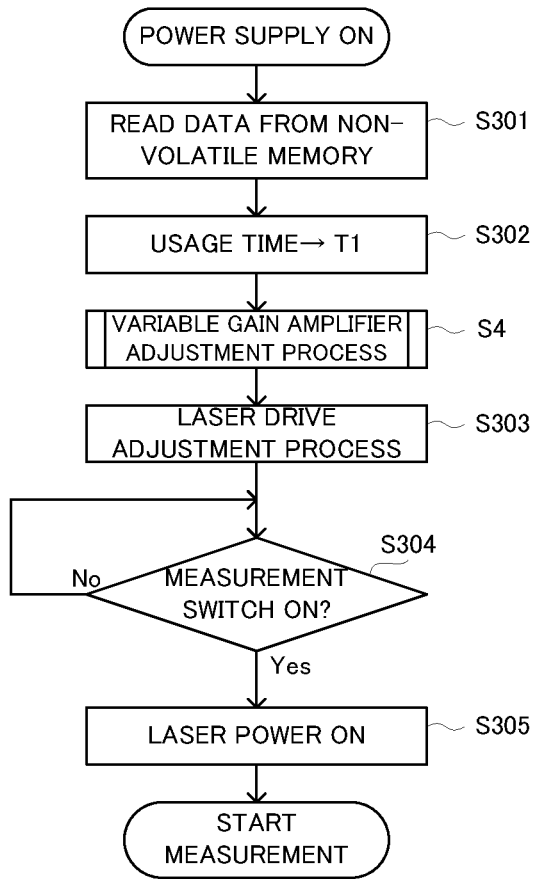
FIG. 9 is a flowchart illustrating an operation process during measurement.

In FIG. 9, firstly, the CPU 11 of the main body portion 10 reads the probe data stored in the non-volatile memory 25 of the probe portion 20 (step S301). The CPU 11 then stores a counter value T1 in the register within the CPU 11 on the basis of the usage time included in the probe data (step S302). The "usage time" according to the example means total lighting hours of the light source 21. For example, if the usage time is 100 hours, the counter value T1 is "100".

The CPU 11 then controls the variable gain amplifier 15 on the basis of the variable gain amplifier adjustment value included in the probe data (step S4). Now, the process in the step S4 will be explained with reference to the flowchart in FIG. 10.

Figure 10:
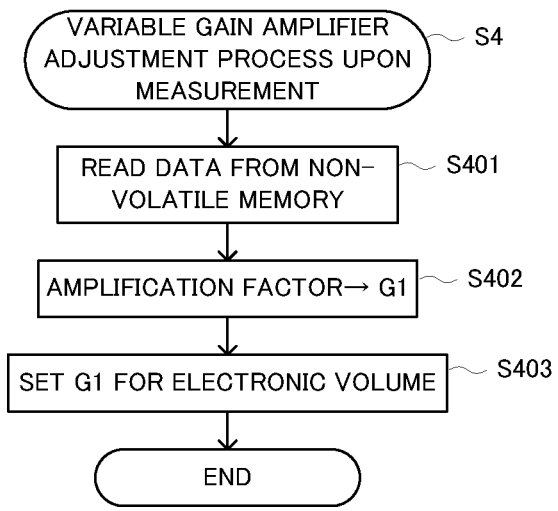
FIG. 10 is a flowchart illustrating a variable gain amplifier adjustment process during measurement.

In FIG. 10, the CPU 11 reads the probe data stored in the non-volatile memory 25 of the probe portion 20 (step S401), and then sets "G1" as the setting value associated with the variable gain amplifier 15 on the basis of the variable amplified adjustment value included in the probe data (step S402). The CPU 11 then sets G1 for the electronic volume of the variable gain amplifier 15 (step S403).

Back in FIG. 9 again, after the aforementioned step S4, the CPU 11 controls the laser drive circuit 12 on the basis of the laser drive adjustment value included in the probe data (step S303). The CPU 11 then determines whether or not a measurement switch (not illustrated) of the measuring apparatus 100 is set to be in an ON state (step S304).

If it is determined that the measurement switch is not set to be in the ON state (i.e. is in an OFF state) (the step S304: No), the CPU 11 performs the process in the step S304 again (i.e. becomes in a standby state. On the other hand, if it is determined that the measurement switch is set to be in the ON state (the step S304: Yes), the CPU 11 controls the laser drive circuit 12 to supply the drive current to the light source 21 of the probe portion 20 (step S305).

Next, a process of updating the usage time after the start of the measurement (i.e. the total lighting hours of the light source 21) will be explained with reference to the flowchart in FIG. 11.

Figure 11:
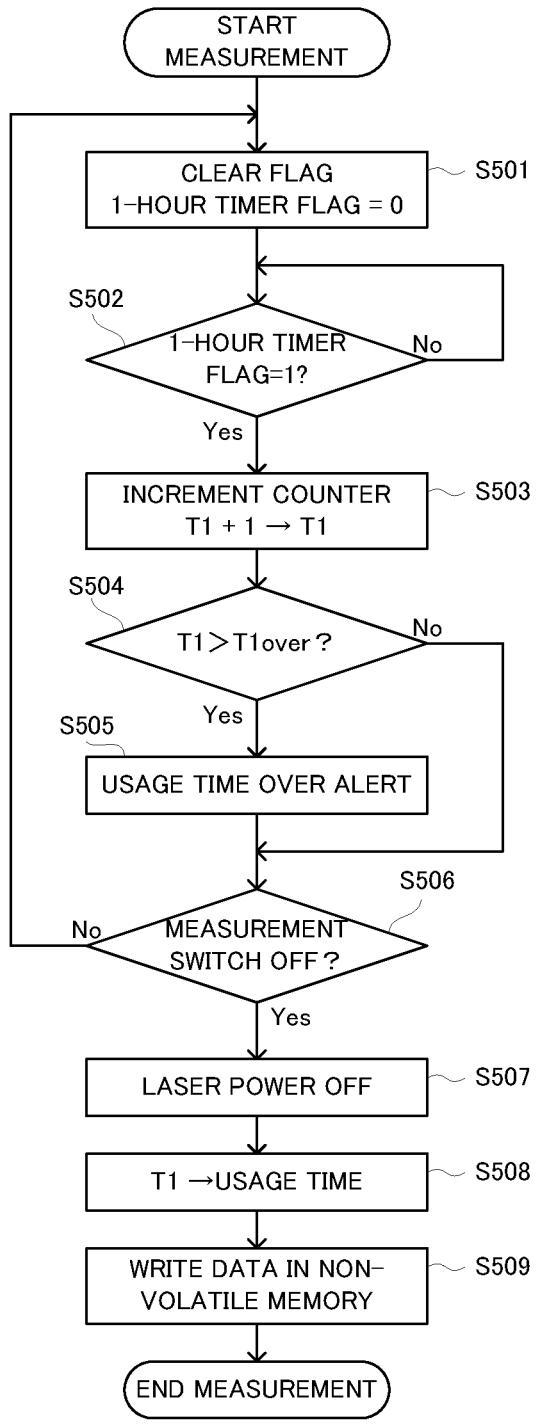
FIG. 11 is a flowchart illustrating a use time updating process.

In FIG. 11, firstly, the CPU 11 clears a 1-hour timer flag and starts a timer program (step S501). The timer program is configured to set the 1-hour timer flag after a lapse of one hour.

The CPU 11 then determines whether or not a value of the 1-hour timer flag is "1" (i.e. one hour has passed) (step S502). If it is determined that the value of the 1-hour timer flag is not "1" (the step S502: No), the CPU 11 performs the process in the step S502 again. On the other hand, if it is determined that the value of the 1-hour timer flag is "1" (the step S502: Yes), the CPU 11 increments the counter value T1 and stores it in the register within the CPU 11 (step S503).

The CPU 11 then determines whether or not the counter value T1 exceeds a specified value T1over, which is, for example, 500 hours or the like (step S504). If it is determined that the counter T1 does not exceed the specified value T1over (the step S504: No), the CPU 11 performs a process in a step 506 described later. On the other hand, if it is determined that the counter T1 exceeds the specified value T1over (the step S504: Yes), the CPU 11 displays, for example, an alert or the like indicating the excess of the usage time on the display 14 (step S505).

The CPU 11 then determines whether or not the measurement switch of the measuring apparatus 100 is set to be in the OFF state (step S506). If it is determined that the measurement switch is not set to be in the OFF set (i.e. is in the ON state) (the step S506: No), the CPU 11 performs the process in the step S501.

On the other hand, if it is determined that the measurement switch is set to be in the OFF state (the step 506: Yes), the CPU 11 controls the laser drive circuit 12 not to supply the drive current to the light source 21 of the probe portion 20 (step S507). The CPU 11 then sets the counter value T1 as the usage time (step S508), and writes it in the non-volatile memory 25 of the probe portion 20 (step S509).

Second Example

Figure 12:
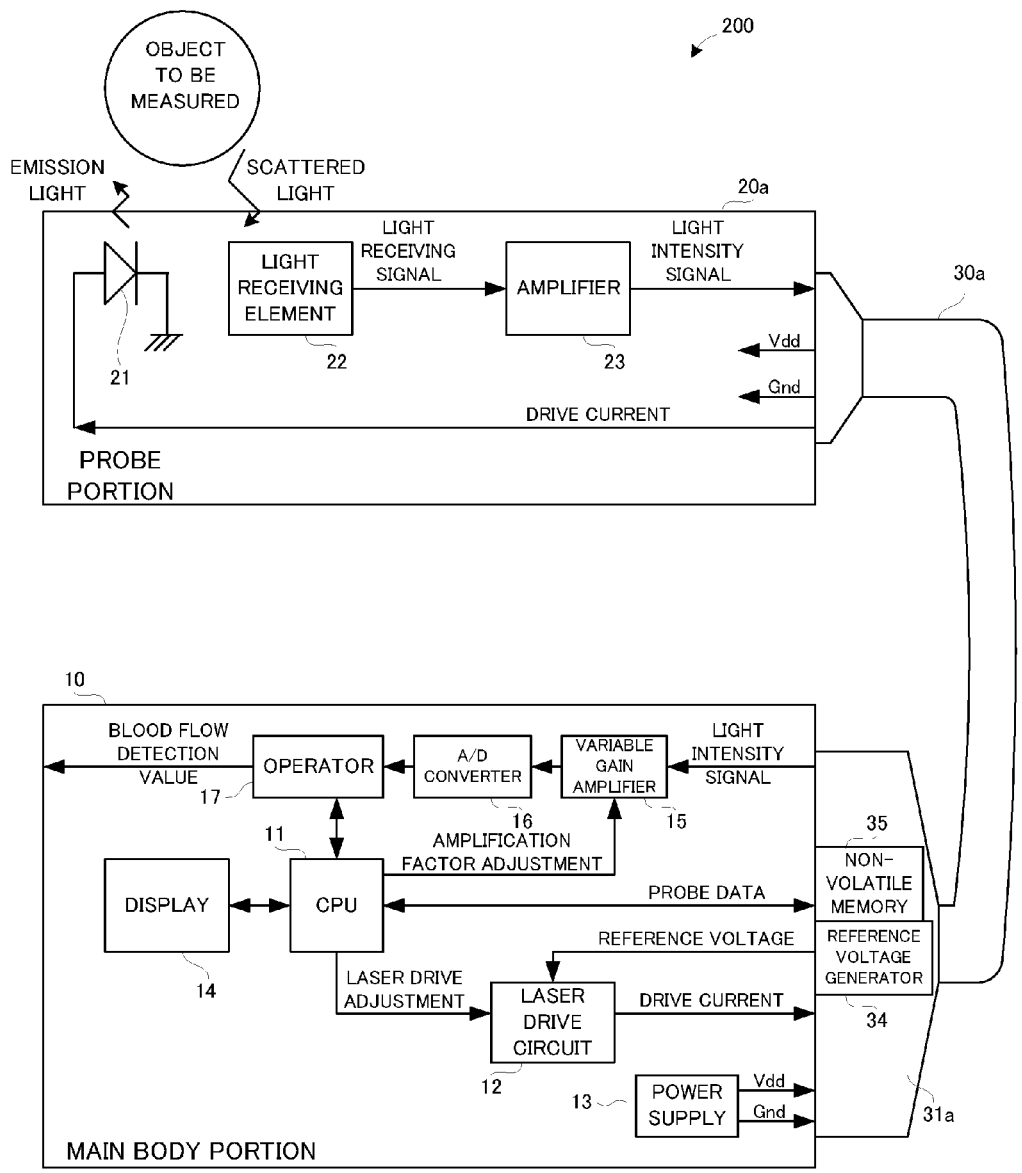
FIG. 12 is a block diagram illustrating a configuration of a measuring apparatus according to a second example.

A second example according to the measuring apparatus of the present invention will be explained with reference to FIG. 12. The second example is the same as the first example, except that the configuration of the probe portion and the connecting cable is partially different. Thus, a repetitive explanation will be omitted, and the same portions on the drawings will carry the same reference numerals. Basically, only different portions from those in the first example will be explained with reference to FIG. 12. FIG. 12 is a block diagram illustrating a configuration of a measuring apparatus according to the second example.

In FIG. 12, a measuring apparatus 200 is provided with the main body portion 10, a probe portion 20a, and a connecting cable 30a configured to electrically connect the main body portion 10 and the probe portion 20a to each other. The connecting cable 30a is formed integrally with the probe portion 20a.

Particularly in the example, a reference voltage generator 34 and a non-volatile memory 35 configured to store therein the probe data are built in a connector 31a of the connecting cable 30a. By virtue of such a configuration, it is possible to miniaturize and lighten the probe portion 20a, which is extremely useful in practice.

Third Example

Figure 13:
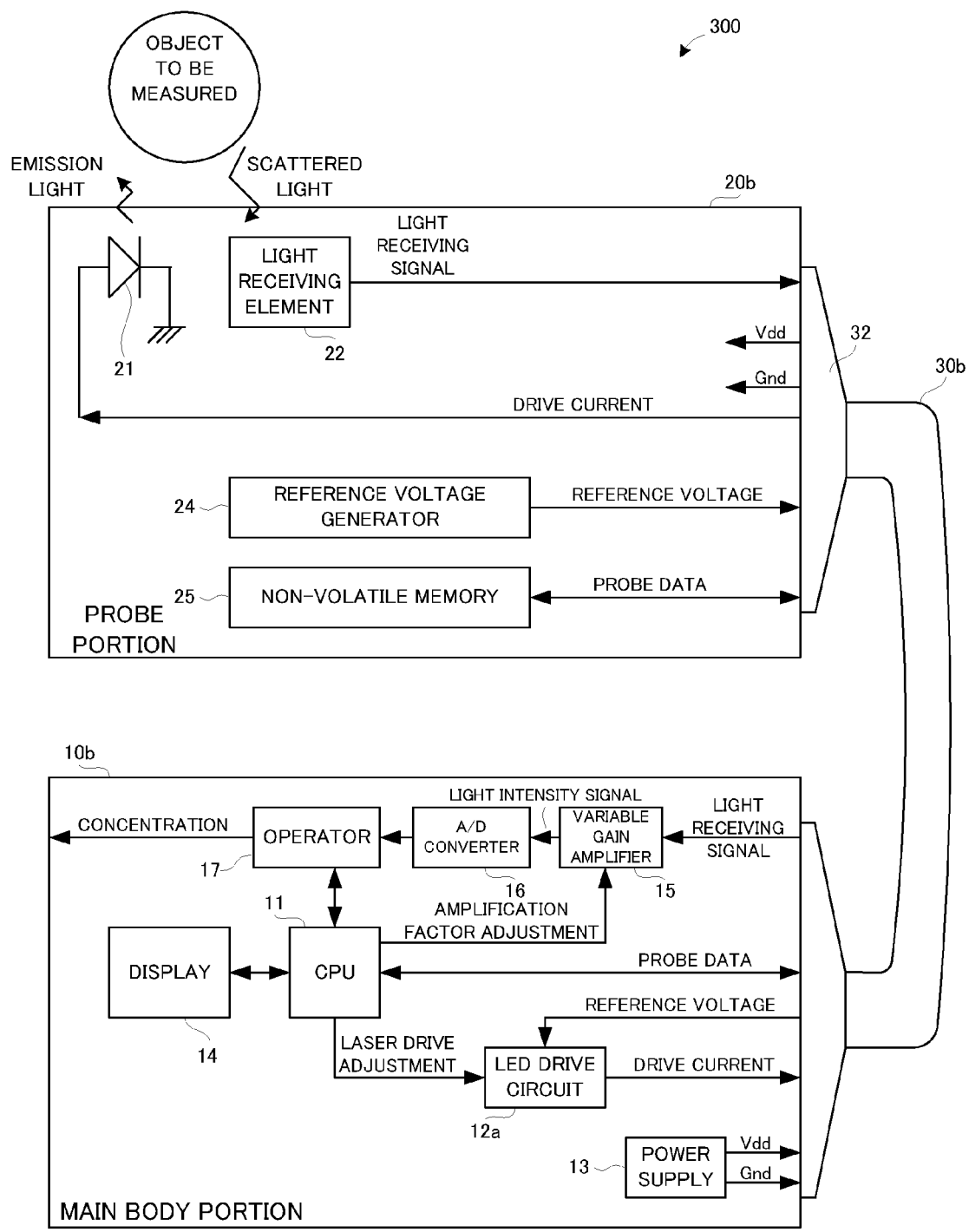
FIG. 13 is a block diagram illustrating a configuration of a measuring apparatus according to a third example.

A third example according to the measuring apparatus of the present invention will be explained with reference to FIG. 13. The third example is the same as the first example, except that the configuration of the measuring apparatus is partially different. Thus, a repetitive explanation will be omitted, and the same portions on the drawings will carry the same reference numerals. Basically, only different portions from those in the first example will be explained with reference to FIG. 13. FIG. 13 is a block diagram illustrating a configuration of a measuring apparatus according to the third example.

In FIG. 13, a measuring apparatus 300 is provided with a main body portion 10b, a probe portion 20b, and a connecting cable 30b configured to electrically connect the main body portion 10b and the probe portion 20b to each other. The connecting cable 30b is formed integrally with the main body portion 10b. A connector 32 of the connecting cable 30b is formed detachably from the probe portion 20b.

In the example, a light emitting diode (LED) is used as the light source 21 of the probe portion 20b. Moreover, a light receiving signal outputted from the light receiving element 22 of the probe portion 20b is transmitted to the variable gain amplifier 15 of the main body portion 10b via the connecting cable 30b. The main body portion 10b is provided with a LED drive circuit 12a, in response to the light emitting diode adopted as the light source 21 of the probe portion 20b.

In the example, for example, blood flowing through a transparent tube, which constitutes an external blood circuit, is the object to be measured. Then, the operator 17 of the main body portion 10b estimates blood concentration, from an intensity change in the data quantized by the A/D converter 16. Since various known aspects can be applied to a method of estimating the blood concentration, an explanation of the details will be omitted.

Instead of the light emitting diode, for example, a semiconductor laser or the like can be also applied to the light source 21.

Fourth Example

Figure 14:
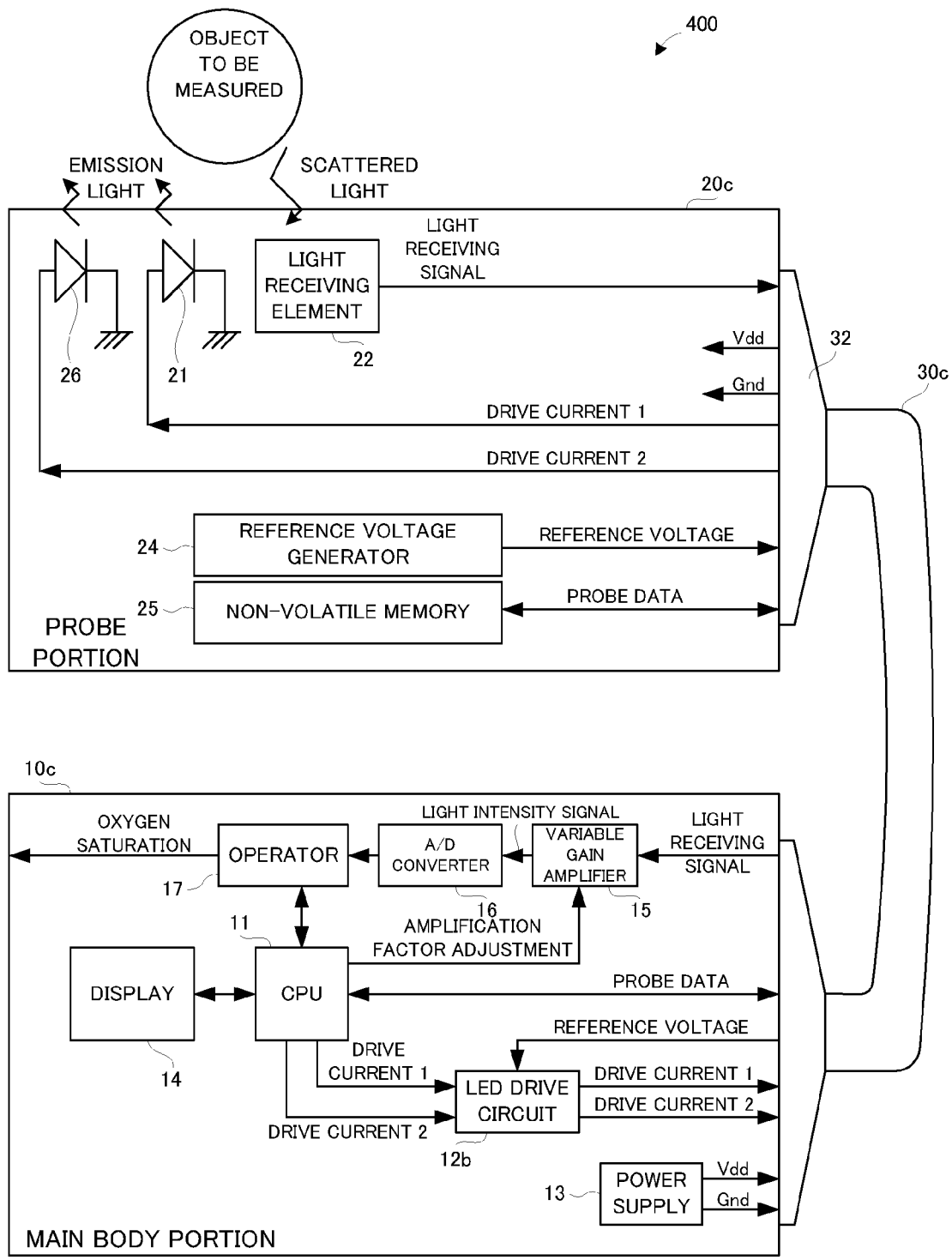
FIG. 14 is a block diagram illustrating a configuration of a measuring apparatus according to a fourth example.

A fourth example according to the measuring apparatus of the present invention will be explained with reference to FIG. 14. The fourth example is the same as the first example, except that the configuration of the measuring apparatus is partially different. Thus, a repetitive explanation will be omitted, and the same portions on the drawings will carry the same reference numerals. Basically, only different portions from those in the first example will be explained with reference to FIG. 14. FIG. 14 is a block diagram illustrating a configuration of a measuring apparatus according to the fourth example.

In FIG. 14, a measuring apparatus 400 is provided with a main body portion 10c, a probe portion 20c, and a connecting cable 30c configured to electrically connect the main body portion 10c and the probe portion 20c to each other. The connecting cable 30c is formed integrally with the main body portion 10c. A connector 32 of the connecting cable 30c is formed detachably from the probe portion 20c.

In the example, the probe portion 20c is provided with two light sources 21 and 26. As the light sources 21 and 26, light emitting diodes with wavelengths different from each other are used. Moreover, a light receiving signal outputted from the light receiving element 22 of the probe portion 20c is transmitted to the variable gain amplifier 15 of the main body portion 10c via the connecting cable 30c. The probe data stored in the non-volatile memory 25 includes a LED drive adjustment value corresponding to the light source 21 and a LED drive adjustment value corresponding to the light source 26.

The main body portion 10c is provided with a LED drive circuit 12b, in response to the light emitting diodes adopted as the light sources 21 and 26 of the probe portion 20c. The LED drive circuit 12b is configured to output a drive current 1 for driving the light source 21 and a drive current 2 for driving the light source 26. Moreover, the CPU 11 controls the LED drive circuit 12b on the basis of both the LED drive adjustment value corresponding to the light source 21 and the LED drive adjustment value corresponding to the light source 26.

The operator 17 of the main body portion 10c estimates oxygen saturation in the blood, from the intensity change of the data quantized by the A/D converter 16. Since various known aspects can be applied to a method of estimating the oxygen saturation in the blood, an explanation of the details will be omitted.

The present invention is not limited to the aforementioned embodiments and examples, but various changes may be made, if desired, without departing from the essence or spirit of the invention which can be read from the claims and the entire specification. A measuring apparatus, a probe portion, and a connecting cable which involve such changes are also intended to be within the technical scope of the present invention.

DESCRIPTION OF REFERENCE NUMERALS 10, 10b, 10c main body portion
11 CPU
12 laser drive circuit
12a, 12b LED drive circuit
13 power supply
14 display
15 variable gain amplifier
16 A/D converter
17 operator
20, 20a, 20b, 20c probe portion
21, 26 light source
22 light receiving element
23 amplifier
24 reference voltage generator
25 non-volatile memory 30, 30a, 30b, 30c connecting cable
31, 31a, 32 connector
100, 200, 300, 400 measuring apparatus

The invention claimed is:

1. A measuring apparatus of an optical type comprising a probe portion and a main body portion, which are electrically connected to each other by a connecting cable, said probe portion having:
a light source;
a reference voltage generating device configured to apply predetermined reference voltage to said main body portion; and
a storing device configured to store therein current adjustment information, which is information for adjusting a drive current to be supplied to the light source, said main body portion having:
a drive current supplying device configured to supply the drive current to the light source, due to the applied reference voltage; and
a controlling device configured to control the drive current supplying device in such a manner that the drive current has a drive current value to be supplied to the light source, on the basis of the stored current adjustment information, wherein said connecting cable is formed integrally with said probe portion, and has a connector at one end of said connecting cable configured to be attached to or be detached from said main body portion.

2. The measuring apparatus according to claim 1, wherein the storing device further stores therein usage time information, which is information indicating a usage time of said probe portion.

3. The measuring apparatus according to claim 2, wherein the controlling device updates the usage time information, according to an operating time of said measuring apparatus.

4. The measuring apparatus according to claim 2, wherein said main body portion further has a notifying device configured to notify a user of said measuring device if the usage time indicated by the stored usage time information is greater than a predetermined value.

5. The measuring apparatus according to claim 1, wherein said measuring apparatus is a blood flow detecting apparatus.

* * * * *